(12) United States Patent
Dubertret et al.

(10) Patent No.: US 7,951,453 B2
(45) Date of Patent: *May 31, 2011

(54) WATER SOLUBLE METAL AND SEMICONDUCTOR NANOPARTICLE COMPLEXES

(75) Inventors: Benoit Dubertret, New York, NY (US); Vincent Noireaux, New York, NY (US); Albert Libchaber, New York, NY (US)

(73) Assignee: The Rockefeller University, New York, NY (US)

( * ) Notice: Subject to any disclaimer, the term of this patent is extended or adjusted under 35 U.S.C. 154(b) by 479 days.

This patent is subject to a terminal disclaimer.

(21) Appl. No.: 11/981,439

(22) Filed: Oct. 31, 2007

(65) Prior Publication Data

US 2008/0193762 A1 Aug. 14, 2008

Related U.S. Application Data

(62) Division of application No. 10/219,440, filed on Aug. 15, 2002.

(51) Int. Cl.
*A61K 9/50* (2006.01)

(52) U.S. Cl. .............. 428/402.24; 428/403; 436/73; 436/829; 424/450; 427/215; 427/220

(58) Field of Classification Search ............ 424/9.5, 424/450; 252/301.4; 428/402; 427/213.3; 264/4; 436/73, 829
See application file for complete search history.

(56) References Cited

U.S. PATENT DOCUMENTS

| | | | |
|---|---|---|---|
| 5,277,913 A | 1/1994 | Thompson et al. | |
| 5,817,856 A | 10/1998 | Tirosh | |
| 5,846,517 A | 12/1998 | Unger | |
| 5,990,479 A | 11/1999 | Weiss et al. | |
| 6,036,886 A | 3/2000 | Chhabra et al. | |
| 6,207,392 B1 | 3/2001 | Weiss et al. | |
| 6,251,303 B1 | 6/2001 | Bawendi et al. | |
| 6,274,323 B1 | 8/2001 | Bruchez et al. | |
| 6,306,610 B1 | 10/2001 | Bawendi et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,423,551 B1 | 7/2002 | Weiss et al. | |
| 6,444,143 B2 | 9/2002 | Bawendi et al. | |
| 2001/0031473 A1* | 10/2001 | Dattagupta et al. | 435/6 |

FOREIGN PATENT DOCUMENTS

| | | |
|---|---|---|
| WO | WO9724224 A | 7/1997 |
| WO | WO 01/33223 A1 | 5/2001 |
| WO | WO 01/33224 A1 | 5/2001 |

OTHER PUBLICATIONS

*Quantum Dot Vision* Mar. 2003, 1(1):1-15.
Salvatore Belsito, et al., "Molecular and Mesoscopic Properties of Hydrophilic Polymer-Grafted Phospholipids Mixed with Phosphatidylcholine in Aqueous Dispersion: Interaction of Dipalmitoyl N-Poly(Ethylene Glycol)Phosphatidylethanolamine with Dipalmitoylphosphatidylcholine Studied by Spectrophotometry and Spin-Label Electron Spin Resonance", *Biophysical Journal* 2000, 78:1420-1430.
D Bhadra, et al., "Pegnology: a review of PEG-ylated systems", *Pharmazie* 2002, 57(1):5-29.
Stephan Förster, et al., "From Self-Organizing Polymers to Nanohybrid and Biomaterials", *Angew. Chem. Int. Ed.* 2002, 41:688-714.
Markus Johnsson, et al., "Spherical Micelles and Other Self-Assembled Structures in Dilute Aqueous Mixtures of Poly(Ethylene Glycol) Lipids", *J. Phys. Chem. B.* 2001, 105:8420-8430.
Marie-Christine Jones, et al., "Polymeric micelles—a new generation of colloidal drug carriers", *European Journal of Pharmaceutics and Biopharmaceutics* 1999, 48:101-111.
Glen S. Kwon, "Diblock Copolymer Nanoparticles for Drug Delivery", *Critical Reviews™ in Therapeutic Drug Carrier Systems* 1998, 15(5):481-512.
Vladimir P. Torchilin, "PEG-based micelles as carriers of contrast agents for different imaging modalities", *Advanced Drug Delivery Reviews* 2002, 54:235-252.
Shen Lifen et al., "Bilayer Surfactant Stabilized Magnetic Fluids: Synthesis and Interactions at Interfaces", Langmuir, 15:2, 447-453 (1999).
Moffitt et al., Spherical Assemblies of Semiconductor Nanoparticles in Water-Soluble Block copolymer Aggregates, Chem. Mater., vol. 10, 1021-1028 (1998).

* cited by examiner

*Primary Examiner* — James Seidleck
*Assistant Examiner* — Saira Haider
(74) *Attorney, Agent, or Firm* — Hoffmann & Baron, LLP

(57) ABSTRACT

The invention provides a water soluble complex comprising an inner core of a metal or semi-conductor nanoparticle. The nanoparticle is coated with a hydrophobic ligand, which is encapsulated in a micelle. In an aqueous medium, the micelle comprises a hydrophilic shell and a hydrophobic core, the hydrophilic shell comprising a plurality of hydrophilic moieties, the hydrophobic core comprising a plurality of hydrophobic moieties, each hydrophobic moiety comprising at least one chain, each chain comprising a minimum of 8 atoms; wherein the total number of atoms in all chains for each moiety comprises at least 24 atoms. The micelle has a minimum average diameter of approximately 5 nm and a maximum average diameter of approximately 45 nm.

29 Claims, 10 Drawing Sheets

WATER SOLUBLE METAL AND SEMICONDUCTOR NANOPARTICLE COMPLEXES

CROSS REFERENCE TO RELATED APPLICATIONS

This application is a Divisional Application of co-pending U.S. application Ser. No. 10/219,440, filed on Aug. 15, 2002.

BACKGROUND OR THE INVENTION

Organic dyes, such as fluorescent molecules, have been used to label biological materials. These fluorochromes, however, have several disadvantages. For example, fluorochromes generally have narrow wavelength bands of absorption (e.g., about 30-50 nm), broad wavelength bands of emission (e.g., about 100 nm), and broad tails of emission (e.g., another 100 nm) on the red side of the spectrum. Due to the wavelength properties of these fluorophores, the ability to use a plurality of different colored fluorescent molecules is severely impaired. Furthermore, the fluorescence is extremely susceptible to photobleaching.

Nanometer-size semiconductor particles (nanoparticles) are particles which demonstrate quantum confinement effects in their luminescent properties. These semiconductor nanoparticles are also known as "quantum dots." Colloidal particles containing quantum dots can be excited by a single excitation source to provide extremely robust, broadly tunable nanoemitters. In addition, the nanoparticles exhibit optical properties which are superior to that of organic dyes. Therefore, due to their distinctive luminescent properties, quantum dots have the potential to dramatically improve the use of fluorescent markers in biological studies.

However, before nanoparticles can be widely used as biological labels, they must maintain several key properties under aqueous biological conditions: solubility, low toxicity, efficient fluorescence, colloidal stability, and low non-specific adsorption. Unfortunately, despite recent advances, these conditions have not been simultaneously satisfied by the prior art. Not surprisingly, no reports have demonstrated in vivo applications of semiconductor nanoparticles.

It has proven especially difficult to render semiconductor nanoparticles soluble in water. Currently, the main strategy to solubilize (e.g., dissolve) semiconductor nanoparticles in water is to exchange the hydrophobic ligands (e.g., organic moieties which are insoluble in water) present after synthesis of the semiconductor nanoparticles with thiolated hydrophilic ligands. Two approaches have been used.

In the first approach, the hydrophobic ligands surrounding the nanoparticle are exchanged by a monolayer of ligands which is constituted of a thiol group at one end that binds to the nanoparticle surface and a hydrophilic group at the other end (Chan et al. *Science* (1998) 281:2016; Mikulec, F. PhD. thesis at the Massachusetts Institute of Technology, 1999; Bawendi et al. U.S. Pat. No. 6,319,426 B1). However, this process yielded semiconductor nanoparticles with poor stability.

In the other approach, the hydrophobic ligands are exchanged by a multilayered shell of crosslinked silanes (Bruchez et al. Science (1998) 281:2013). One disadvantage to this approach is the long amount of time it takes to exchange the hydrophobic ligands with crosslinked silanes. In addition, the soluble semiconductor nanoparticles exhibit high non-specific adsorption (e.g., the soluble semiconductor nanoparticles aggregate in biological systems).

The use of micelles to solubilize semiconductor nanoparticles in water is disclosed in U.S. Pat. No. 6,319,426 B1 to Bawendi et al. A micelle is typically a colloidal aggregate of amphiphilic substances. Generally, in aqueous medium, the nonpolar (e.g., hydrophobic) ends of the amphiphilic substance face inward and the polar (e.g., hydrophilic) tails face outward. This orientation of the amphiphilic substance results in a micelle having a hydrophobic core and a hydrophilic shell. Thus, unfavorable contacts between water and the hydrophobic tails are eliminated.

The micelles disclosed in the Bawendi et al. patent are formed using sodium dioctyl sulfosuccinate (AOT) or Brij surfactants. The AOT reagent contains two short hydrophobic chains (each chain containing eight carbon atoms) and an ion for the hydrophilic portion. The Brij surfactants contain block copolymers that have a long hydrophilic polyethylene glycol chain and one long hydrophobic hydrocarbon chain (containing twelve or eighteen carbon atoms). However, the micelles that are formed using the reagents disclosed in the Bawendi et al. patent are not stable in aqueous solutions.

Therefore, there is a need for stable, water soluble semiconductor nanoparticles, which can be used in biological applications, both in vitro and in vivo. The absorption and emission properties of the stable, water soluble semiconductor nanoparticles offer advantages over current conventional organic dyes.

SUMMARY OF THE INVENTION

These and other objective have been met by providing a water soluble complex comprising an inner core of a metal or semi-conductor nanoparticle. The nanoparticle is coated with a hydrophobic ligand, which is encapsulated in a micelle. In an aqueous medium, the micelle comprises a hydrophilic shell and a hydrophobic core, the hydrophilic shell comprising a plurality of hydrophilic moieties, the hydrophobic core comprising a plurality of hydrophobic moieties, each hydrophobic moiety comprising at least one chain, each chain comprising a minimum of 8 atoms; wherein the total number of atoms in all chains for each moiety comprises at least 24 atoms. Furthermore, the micelle has a minimum average diameter of approximately 5 nm and a maximum average diameter of approximately 45 nm.

In another embodiment, the invention provides a method for determining the progeny of a target cell in a mixture of cells. The method comprises introducing at least two complexes into the target cell; allowing the target cell to replicate; and observing the cells that comprise the complex in the mixture of cells, wherein the cells that comprise the complex constitute the progeny of the target cell.

In a further embodiment, the invention provides a conjugate comprising a complex and a biological molecule.

DETAILED DESCRIPTION OF THE INVENTION

Figure 1A:
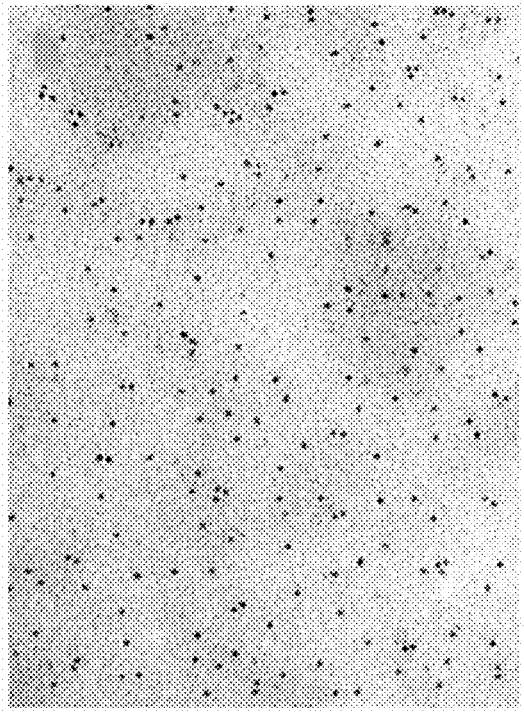
FIG. 1: Characterization of water soluble complexes. (A) Transmission electron microscopy (JEOL 100 cx electron microscope at 80 kV) of water soluble complexes dried on a carbon-formvar coated 200 mesh nickel grid. Only the semiconductor nanoparticles inside the micelle core are visible. The particles are evenly spread on the surface of the grid. Most of the nanoparticles are isolated, some packs of two to four nanopaticles are visible. Thus, the majority of micelles contain a single nanoparticle. (B) The phospholipid layer that surrounds the dots can be visualized by negative staining with 1% phosphotungstic acid at pH 7.0. This allows visualization of both the nanoparticle and the micelle. The nanoparticle (dark point) are surrounded by a white halo of unstained phospholipids. The majority of the micelles contain a single nanoparticle.
Figure 1B:
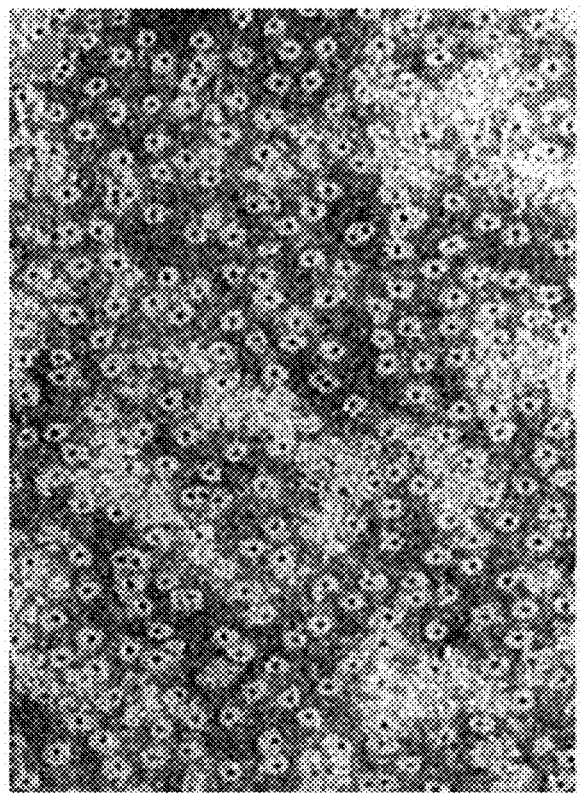

The present invention relates to a water soluble complex comprising a nanoparticle coated with a hydrophobic ligand encapsulated in a micelle. In this specification, the size of various particles and complexes will be measured by their diameters. It will be understood that these diameters are average diameters, unless stated otherwise.

Nanoparticles

In this specification, a "nanometer particle" or "nanoparticle" refers to a metal or semiconductor particle with a diameter in the nanometer (nm) range. The nanoparticles may be any size that can be encapsulated in a micelle having a minimum diameter of approximately 5 nm and a maximum diameter of approximately 45 nm. Preferably, the nanoparticle has a minimum diameter of about 1 nm and a maximum diameter of about 20 nm.

The metal can be any metal, metal oxide, or mixtures thereof. The metal may be any size that can be encapsulated in a micelle having a diameter of approximately 5 nm to approximately 45 nm. Some examples of metals useful in the present invention include gold, silver, platinum, and copper. Examples of metal oxides include iron oxide, titanium oxide, chromium oxide, cobalt oxide, zinc oxide, copper oxide, manganese oxide, and nickel oxide.

The metal or metal oxide can be magnetic. Examples of magnetic metals include, but are not limited to, iron, cobalt, nickel, manganese, and mixtures thereof. An example of a magnetic mixture of metals is a mixture of iron and platinum. Examples of magnetic metal oxides include, for example, iron oxide (e.g., magnetite, hematite) and ferrites (e.g., manganese ferrite, nickel ferrite, or manganese-zinc ferrite).

Preferably, the nanoparticle comprises a semiconductor. The semiconductor is capable of emitting electromagnetic radiation upon excitation. Some examples of semiconductors include Group II-VI, Group III-V, and Group IV semiconductors. The Group II-VI semiconductors include, for example, MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe, and mixtures thereof. Group III-V semiconductors include, for example, GaAs, GaN, GaP, GaSb, InGaAs, InP, InN, InSb, InAs, AlAs, AlP, AlSb, AlS, and mixtures therefore. Group IV semiconductors include, for example, germanium, lead, and silicon.

The semiconductor may also include mixtures of semiconductors from more than one group, including any of the groups mentioned above.

The formation of nanoparticles comprising Group III-V semiconductors is described in U.S. Pat. No. 5,751,018 and U.S. Pat. No. 5,505,928. U.S. Pat. No. 5,262,357 describes Group II-VI and Group III-V semiconductor nanoparticles. These patents also describe the control of the size of the semiconductor nanoparticles during formation using crystal growth terminators. The specifications of U.S. Pat. No. 5,751,018, U.S. Pat. No. 5,505,928, and U.S. Pat. No. 5,262,357 are hereby incorporated by reference.

In one embodiment, the nanoparticles are used in a core/shell configuration. A first semiconductor nanoparticle forms a core ranging in diameter, for example, from about 2 nm to about 10 nm. A shell, of another semiconductor nanoparticle material, grows over the core nanoparticle to a thickness of, for example, 1-10 monolayers. When, for example, a 1-10 monolayer thick shell of CdS is epitaxially grown over a core of CdSe, there is a dramatic increase in the room temperature photoluminescence quantum yield.

The core of a nanoparticle in a core/shell configuration can comprise, for example, MgS, MgSe, MgTe, CaS, CaSe, CaTe, SrS, SrSe, SrTe, BaS, BaTe, BaTe, ZnS, ZnSe, ZnTe, CdS, CdSe, CdTe, HgS, HgSe, HgTe, GaAs, GaN, GaP, GaSb, InGaAs, InP, InN, InSb, InAs, AlAs, AlP, AlSb, AlS, PbS, PbSe, Ge, Si, or mixtures thereof. Examples of semiconductors useful for the shell of the nanoparticle include, ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, or mixtures thereof. Preferably, the core/shell comprises CdSe/CdS, CdSe/ZnS, or CdTe/ZnS. Formation of such core/shell nanoparticles is described more fully in Peng et al., Epitaxial Growth of Highly Luminescent CdSe/CdS Core/Shell Nanoparticles with Photostability and Electronic Accessibility, *Journal of*

*the American Chemical Society*, (1997) 119:7019-7029, the subject matter of which is hereby incorporated by reference.

The semiconductor nanoparticles used in the invention preferably have the capability of absorbing radiation over a broad wavelength band. The wavelength band includes gamma radiation to microwave radiation.

The semiconductor nanoparticles preferably have the capability of emitting radiation within a narrow wavelength band of about 40 nm or less, preferably about 20 nm or less. A narrow emission band permits the simultaneous use of a plurality of differently colored semiconductor nanoparticle complexes with different semiconductor nanoparticles without overlap (or with a small amount of overlap) in wavelengths of emitted light when exposed to the same energy source.

The frequency or wavelength of the narrow wavelength band of light emitted from the semiconductor nanoparticle may be further selected according to the physical properties, such as size, of the semiconductor nanoparticle. The wavelength band of light emitted by the semiconductor nanoparticle, formed using the above embodiment, may be determined by either (1) the size of the core, or (2) the size of the core and the size of the shell, depending on the composition of the core and shell of the semiconductor nanoparticle. For example, a nanoparticle composed of a 2.3 nm diameter core of CdSe and a 1-2 nm thick shell of ZnS will emit a narrow wavelength band of light with a peak intensity wavelength of 490 nm. However, when the CdSe core is 4.2 nm in diameter, the nanoparticle will emit a narrow wavelength band of light with a peak intensity of 570 nm. Furthermore, if the core is composed of a 6 nm diameter core of CdTe, the nanoparticle will emit at 660 nm.

A plurality of alternatives to changing the size of the semiconductor nanoparticles in order to selectably manipulate the emission wavelength of semiconductor nanoparticles exist. These alternatives include: (1) varying the composition of the nanoparticle, and (2) adding a plurality of shells around the core of the nanoparticle in the form of concentric shells. It should be noted that different wavelengths can also be obtained in multiple shell type semiconductor nanoparticles by respectively using different semiconductor nanoparticles in different shells, i.e., by not using the same semiconductor nanoparticle in each of the plurality of concentric shells.

Selection of the emission wavelength by varying the composition, or alloy, of the semiconductor nanoparticle is known in the art. For example, a CdS semiconductor nanoparticle having a emission wavelength of 400 nm may be alloyed with a CdSe semiconductor nanoparticle having an emission wavelength of 530 nm. When a nanoparticle is prepared using an alloy of CdS and CdSe, the wavelength of the emission from a plurality of identically sized nanoparticles may be tuned continuously from 400 nm to 530 nm depending on the ratio of S to Se present in the nanoparticle. The ability to select from different emission wavelengths while maintaining the same size of the semiconductor nanoparticle may be important in applications which require the semiconductor nanoparticles to be uniform in size, or for example, an application which requires all semiconductor nanoparticles to have very small dimensions when used in applications with steric restrictions.

In a preferred embodiment, the semiconductor nanoparticle is fluorescent. The fluorescence of the semiconductor nanoparticle is preferably preserved (e.g., is not quenched).

The nanoparticle is coated with a hydrophobic ligand. The hydrophobic ligand coats the nanoparticle through non-covalent or covalent interactions. An example of a hydrophobic ligand which coats the nanoparticle non-covalently is trioctylphosphine oxide (TOPO).

Some examples of hydrophobic ligands which can coat the nanoparticle covalently include fatty thiols, fatty amines, fatty alcohols, fatty acids, fatty ester groups and mixtures thereof. Such mixtures include, for example, a mixture of oleic acid and oleylamine. If the hydrophobic ligand is a fatty thiol, the alkyl group present in the fatty thiol preferably comprises a minimum of eight and a maximum of twenty carbon atoms.

Micelles

To form a water soluble complex, the hydrophobic ligand coated nanoparticle(s) is encapsulated in a micelle. The micelles of the present invention have a minimum average diameter of about 5 nm and preferably about 9 nm. The maximum average diameter of the micelle is about 45 nm, preferably about 40 nm, more preferably about 35 nm, and most preferably about 15 nm. The size of a micelle depends on several factors including, for example, molecular weight, relative proportion of hydrophilic and hydrophobic moieties, and aggregation number. The micellar size can be determined by any method known to those in the art, such as atomic force microscopy, transmission electron microscopy, and scanning electron microscopy.

The micelles useful in the present invention contain a hydrophobic core and a hydrophilic shell. It is possible to form reverse micelles having a hydrophilic core and a hydrophobic shell. However, these reverse micelles are not included in the present invention.

In an aqueous solution, amphiphilic substances (comprising hydrophobic and hydrophilic moieties) form micelles when the concentration is above a certain critical micelle concentration (cmc). The cmc of the amphiliphilic substance can be determined by any known method in the art. For example, fluorescent probes, such as pyrene, may be used. The cmc can be obtained from a plot of the fluorescence intensity ratio from excitation spectra $I_{333}/I_{338}$ against concentration.

The hydrophobic core of the micelle comprises a plurality of hydrophobic moieties. The number of hydrophobic moieties can be any number that forms a micelle having a diameter of approximately 5 nm to approximately 45 nm.

The hydrophobic moiety comprises at least one chain. The maximum number of chains in the moiety can be any number, such that a plurality of moieties forms a micelle having a diameter of approximately 5 nm to 45 nm. The maximum number of chains will typically not exceed five, more typically three, and most typically two.

The backbone of each chain comprises a minimum of eight atoms. For example, the chain $—CH_2(CH_2)_6CH_3$ contains eight atoms in the backbone of the chain, and $—CH_2(CH_2)_{10}CH_3$ contains twelve atoms in the backbone of the chain.

The maximum number of atoms in the backbone of each chain can be any number that forms a micelle having a diameter of approximately 5 nm to approximately 45 nm. Preferably the maximum number is approximately 1000 atoms.

The total number of atoms in the backbone of all chains comprises at least twenty-four atoms. The chain can be, for example, a fatty hydrocarbon group or a polymer.

If more than one chain is present in a hydrophobic moiety, the chains may be the same as (i.e., homogeneous), or different from (i.e., heterogeneous), each other. For example, when two chains are present in the hydrophobic moiety, both chains can be hexadecyl (i.e., chains are homogeneous). In contrast, one chain can be octadecyl and the other chain can be dodecyl (i.e., chains are heterogeneous). Furthermore, the chains can be heterogeneous and comprise the same number of atoms in the backbone of each chain. For example, when two chains are present in the hydrophobic moiety, one chain can be hexadecyl and the other chain can be hexadecenyl.

The backbone of the chain can comprise any atom or combination of atoms that form chains. Preferably, the backbone of the chain comprises carbon or silicon atoms. An example of a chain which comprises silicon atoms is a polysiloxane chain.

If the backbone of the chain comprises carbon atoms, the chain is preferably a hydrocarbon chain. The hydrocarbon chain may be saturated. Some examples of saturated hydrocarbon chains include n-dodecyl, n-tetradecyl, n-hexadecyl, n-octadecyl, and n-icosyl.

Alternatively, the hydrocarbon chain may comprise one or more double or triple bonds. The maximum number of double or triple bonds is limited only by the length of the chain. For example, a twelve member chain has a maximum of six double or three triple bonds; a fourteen member chain has a maximum of seven double or triple bonds; a eighteen member chains has a maximum of nine double or triple bonds, etc. Each double bond may be in the cis or trans configuration. Some examples of unsaturated chains include oleyl, linoleyl, linolenyl and eleostearyl.

The hydrocarbon chain may be branched. For example, any of the carbon atoms in the hydrocarbon chains described above may further comprise a $C_1$-$C_4$ alkyl, alkenyl, or alkynyl group. Some examples of $C_1$-$C_4$ alkyl, alkenyl, or alkenyl groups include methyl, ethyl, propyl, isopropyl, butyl, isobutyl, butadienyl, isobutenyl, butynyl, etc. Some examples of branched hydrocarbon chains include 3,7,11,15-tetramethylhexadecyl and cis or trans 3,7,11,15-tetramethyl-2-hexadecenyl.

Any of the carbon atoms in any of the hydrocarbon chains described above may further comprise a hydrocarbon ring structure. The hydrocarbon ring may be saturated or unsaturated. Some examples of hydrocarbon rings include cyclopentyl, cyclopentenyl, cyclohexyl, and phenyl. Some examples of hydrocarbon chains further comprising hydrocarbon rings include 1-butyl-4-cyclohexyl-12-dodecyl.

In one embodiment, the hydrophobic moiety of the micelle comprises at least one lipid. Lipids useful in the present invention preferably contain at least two hydrocarbon chains as described above. The hydrocarbon chains are preferably present in a fatty acyl moiety. The fatty acyl moieties in the lipid may contain the same (i.e., homogeneous) hydrocarbon chain or may contain different (i.e., heterogeneous) hydrocarbon chains.

Preferably, the lipid is a phospholipid. The phospholipids may be any glyceryl ester of phosphoric acid wherein the glycerol backbone is further linked by ester bonds to two fatty acyl moieties. In a preferred embodiment, the phosphate group of the phospholipid is bound by a ester link to an ethanolamine. This preferred phospholipid is referred to as 1,2-di(fatty acyl)-sn-glycero-3-phosphoethanolamine, also known as phosphatidylethanolamine (PE). The fatty acyl moieties can be any of the hydrocarbon chains as described above, and may be homogeneous or heterogeneous.

In a further embodiment, the hydrophobic core can further comprise a second hydrophobic moiety. Preferably, the second hydrophobic moiety is a lipid. Preferably, the hydrophobic moiety is 1,2-di(fatty acyl)-sn-glycero-3-phosphocholine (i.e., phosphatidylcholine). The fatty acyl moieties in the phospholipid may comprise any of the hydrocarbon chains as described above and may be homogeneous or heterogeneous.

Examples of hydrophobic polymers include polyglycolide, polylactide, polymethylacrylate, polyvinylbutylether, polystyrene, polycyclopentadienylmethylnorbornene, polyethylenepropylene, polyethylethylene, polyisobutylene, polysiloxane. If the hydrophobic moiety comprises a polymer, the polymer can comprise up to 1000 atoms or more as is known in the art.

The hydrophilic shell comprises a plurality of hydrophilic moieties. The hydrophilic moieties can comprise any moiety which is hydrophilic and/or exhibits low non-specific adsorption. A moiety with low non-specific adsorption preferably has a neutral charge and/or an isoelectric point (pI) close to physiological pH. Preferably, the minimum value for the pI is about 5.0, more preferably about 5.5, and most preferably about 6.0. The maximum value for the pI is about 11.0, more preferably about 10.0, and most preferably about 8.0.

Examples of hydrophilic moieties include hydrophilic polymers. The polymer comprises at least two monomers. The maximum number of monomers can be any number which forms a micelle having a diameter of approximately 5 nm to approximately 45 nm. Preferably, the maximum number of monomers comprising the polymer is 1000, more preferably 900, even more preferably 800, and most preferably 700 monomers.

Each monomer comprises at least one oxygen or nitrogen atom, and may include more, such as two, five, or ten oxygen or nitrogen atoms. Examples of monomers useful in the present invention include N-alkylacrylamide, N,N-dialkylacrylamide, N-isopropylacrylamide, N-methylacrylamide, N-ethylmethacrylamide, N,N-propylacrylamide, N,N-propylmethacrylamide, N-isopropylmethacrylamide, N-cyclopropylacrylamide, N,N-diethylacrylamide, N-methyl-N-isopropylacrylamide, N-methyl-N,N-propylacrylamide, propylene oxide, vinyl ether, hydroxyethyl methacrylate, N-vinylpyrrolidone, amino acids, meth-acrylic acid, N-alkylvinylpyridinium halogenide, styrene sulfonic acid, ethylene glycol, and monosaccharides, such as glucose, galactose, mannose, and fructose.

Examples of polymers include, but are not limited to, polystyrene sulfonic acid, poly-N-alkylvinylpyridinium halogenide, poly(meth)acrylic acid, poly(amino acids), poly-N-vinylpyrrolidone, polyhydroxyethyl methacrylate, polyvinylether, polyethylene glycol, polypropylene oxide, and polysaccharides, such as agarose, dextran, starch, cellulose, amylose, amylopectin, and starch.

In one embodiment, the hydrophilic moiety comprises polyethylene glycol (PEG) or polyethylene imine chains. The polyethylene glycol or polyethylene imine chain can be any molecular mass which can form a micelle having a diameter of approximately 5 to approximately 45 nm. Preferably, the minimum average molecular mass for polyethylene glycol or polyethylene imine is about 350 Da, more preferably about 550 Da, even more preferably about 750 Da, and most preferably about 1000 Da. The maximum average molecular mass for polyethylene glycol or polyethylene imine is about 5000 Da, and more preferably about 2000 Da.

The hydrophilic moiety can be attached to a hydrophobic moiety at any point on a chain of the hydrophobic moiety. Preferably, the hydrophilic moiety is attached at the end of the chain.

In an embodiment, the PEG polymers described above are attached to a lipid. For example, a PEG polymer attached to the phospholipid 1,2-di(fatty acyl)-sn-glycero-3-phosphoethanolamine (PE) forms PEG-PE conjugates. The PEG-PE conjugates can be used to form micelles. The PE moiety can be any of the PE moieties discussed above. In a preferred embodiment, the PE moiety is 1,2-dipalmitoyl-sn-glycero-3-phosphoethanolamine (DPPE).

Various molecular masses of PEG conjugated to PE having fatty acyl moieties of, for example, fourteen, sixteen, and eighteen carbon atoms, can be obtained from Avanti Polar Lipids, Inc.

The hydrophobic core of the PEG-PE micelle described above, can further comprise a second lipid. Preferably, the second lipid is a phospholipid. Examples of phospholipids include 1,2-di(fatty acyl)-sn-glycero-3-phosphocholine, also known as phosphatidylcholine (PC). The fatty acyl moieties in the phospholipid may comprise any of the hydrocarbon chains as described above.

In another embodiment, a hydrophilic polymer can be directly conjugated to a hydrophobic polymer to form a block copolymer. Block copolymers are copolymers in which a monomer of one type is grouped together (block) and joined to another group of monomers of a different type (another block). These block copolymers form polymeric micelles which exhibit a core-shell structure.

The block copolymers can contain two, three, or more blocks, known as diblock, triblock, and multiblock copolymers, respectively. The maximum number of blocks for a multiblock copolymer can be any number which forms a micelle with a diameter of approximately 5 nm to approximately 45 nm.

The blocks can, for example, be in a linear or star arrangement. In a linear arrangement, the blocks are connected end-to-end. In a star arrangement, the blocks are connected via one of their ends at a single junction.

The number of monomer types in a block copolymer may be less than or equal to the number of blocks. For example, a linear triblock polymer can contain three monomer types (e.g., block 1 containing monomer A, block 2 containing monomer B, and block 3 containing monomer C) or two monomer types (e.g., block 1 containing monomer A, block 2 containing monomer B, and block 3 containing monomer A).

The block copolymer can be any block copolymer which forms a polymeric micelle with a hydrophobic core and a hydrophilic shell in accordance with the invention. The monomers and polymers which can be used in a block copolymer include those described above.

The micelle can be functionalized by attaching a chemical linker. The chemical linker can be attached anywhere on the micelle, such as, for example, on the hydrophobic moiety (e.g., phospholipids), hydrophilic moiety (e.g., polyethylene glycol), or combinations thereof. The chemical linker can be attached by any known method in the art. Preferably, the linker is attached to the hydrophilic moiety.

The chemical linker comprises a moiety capable of combining with biological molecules. Examples of such moieties include, but are not limited to, amino, thiol, carboxyl, hydroxyl, succinimidyl, maleimidyl, biotin, aldehyde, and nitrilotriacetic moieties.

The biological molecule can be any biological molecule. Examples of biological molecules, include DNA, RNA, and molecules which comprise amino acid sequences such as peptides, polypeptides, and proteins.

The biological molecule can be linked to the chemical moiety by any known method in the art. For example, the biological molecule can be linked to the hydrophilic shell of the micelle through a thiol or amine group present on the biological molecule. The coupling reaction can involve an heterobifunctional coupler, such as SMCC (succinimidyl 4-N-maleimidomethyl)cyclohexane-1-carboxylate) or EDC (1-ethyl-3-[dimethylaminopropyl]carbodiimide hydrochloride) available from Pierce Biotechnology Inc.

Functionalized PEG lipids, such as PEG-dipalmitoylphosphoethanolamine comprising chemical moieties, such as carboxy NHS ester, maleimide, PDP, amine, and biotin attached to PEG, are commercially available from Avanti Polar Lipids Inc.

Complexes

As stated above, the micelle encapsulates nanoparticles coated with a hydrophobic ligand to form a water soluble complex. The inner core of the complex comprises at least one nanoparticle. The maximum number of nanoparticles can be any number that fits into the inner core of the complex. Preferably, the inner core contains a maximum of about 20 nanoparticles, preferably about 50, more preferably about 100, even more preferably about 500, and most preferably about 1000 nanoparticles.

The nanoparticles in the inner core of the complex can have at least two different diameters. The number of different diameters may be any number, such that the nanoparticles fit into the inner core of the complex. The ability to use different diameters of nanoparticles allows for emission of different wavelengths.

If more than one nanoparticle is present in the inner core of the complex, the complex can comprise at least two different nanoparticles. The number of different nanoparticles used can by any number, such that the nanoparticles fit into the inner core of the complex. The ability to use combinations of different nanoparticles in the inner core allows for a greater array of emission wavelengths.

The complexes are preferably biocompatible. A complex is typically considered biocompatible if it is non-toxic in vivo and has low non-specific adsorption. Non-toxic in vivo is defined as having no adverse effects on the cells of an organism. For example, the phenotype and/or biological functions of the organism is not adversely affected.

Low non-specific adsorption is defined as little or no aggregation (e.g., non-specific interaction) of the complexes with each other or other molecules (e.g., proteins). The aggregation can occur as a result of, for example, electrostatic interactions, ionic interaction, van der Waal forces, and hydrogen bonding forces.

Utility

Due to the non-toxicity and low non-specific adsorption property of the complexes, numerous in vivo and in vitro applications of the complexes are possible.

The complexes fulfill two criteria which render them useful in the biology of a living system. The first criteria is that the nanoparticle-micelles complexes are neutral (e.g., no biological activity of their own or toxicity for their host organism). In addition, the nanoparticle-micelle complexes are stable for a long period of time.

For example, the complexes can be introduced into a target cell in a mixture of cells to determine the progeny (lineage) of the target cell. Therefore, the cell type that the target cell differentiates into can be determined.

The target cell can be any progenitor cell. The progenitor cell can be any cell which gives rise to differentiated cells. Examples of progenitor cells include stem cells, hemopoietic cells, and embryonic cells, such as blastomers.

The target cell can be present in a mixture of cells. The mixture of cells can constitute cells in culture or a non-human organism, such as, for example, a tadpole, mouse, etc. When the mixture of cells constitutes an organism, the mixture of cells is typically an embryo.

The complexes can be introduced into a target cell by any method known to those skilled in the art. For example, the complexes can be microinjected into the target cell. It is preferable to introduce at least two complexes into the target cell. Therefore, when the target cell is allowed to replicate, the complexes are approximately equally distributed among the daughter cells. The conditions used to allow the target cell to replicate are known to those skilled in the art. The cells that comprise the complexes in the mixture of cells constitute the progeny of the target cell.

Example 6 illustrates the method of determining cell lineage. Briefly, water-soluble complexes were injected into one cell of a two cell *Xenopus* embryo. During embryonic development, the fluorescence of the nanoparticle was confined only to the progeny of the injected cell (e.g., only half of the cells of the embryo was labeled).

Example 6 also assessed the toxicity of the complexes by evaluating changes in the phenotype of the host organism as a whole. This is a very stringent criterium that cannot be necessarily measured in cell cultures because small changes that occur in cell culture may be inconsequential. In contrast, the embryo is less forgiving. Cellular perturbances in an embryo have a more global impact and translate into measurable biological phenotypes.

The complexes demonstrated very little toxicity or activity. For example, when a low concentration (e.g., below an OD at 300 nm of 4.0 for 1.5 nl) of the complexes (from Example 1) was injected into *Xenopus* embryos, the toxicity of the complexes was sufficiently low to enable tracing of cell lineage using fluorescence visualization (see Example 6). At high concentration of the complexes (e.g., above an OD at 300 nm of 20.0 for 1.5 nl of complexes), the rate of defective or dead embryos increased. However, at low concentrations, the health of the embryo is statistically similar to uninjected embryos (Table 1).

TABLE

Toxicity of Low Concentration of Complexes Injected into One Cell of An Eight Cell *Xenopus* Embryo With Visualization at Stage 19-20.

|  | Injected with Complexes (1.5 nl injected in 1 cell of an 8 cell stage embryo) N = 55 | Control N = 39 |
| --- | --- | --- |
| Normal | 38 (69%) | 27 (70%) |
| Defects | 15 (27%) | 12 (30%) |
| Dead | 2 (4%) | 0 (0%) |

The second criteria, stability of the complexes, is demonstrated in Example 6 and 7. The stability of the nanoparticle-micelle is measured by its degree of aggregation and the evolution of the fluorescence of the nanoparticle. The complexes did not exhibit any visible aggregation after four days of embryonic development. When complexes were injected into a *Xenopus* embryo at a two-cell stage, fluorescence was still detectable at the tadpole stage (see Example 6). Furthermore, the complexes are extremely resistance to photobleaching (see Example 7).

Thus, Examples 6 and 7 show that the nanoparticle-complexes are biologically compatible for in vivo applications.

Other applications for the complexes include, for example, cell sorting. The cells of interest, in a mixture of cells, can be labeled with the complexes of the present invention. The cells can then be sorted by, for example, a magnetic field or flow cytometry (e.g., fluorescence activated cell sorting (FACS)).

When sorting with a magnetic field, the nanoparticles in the complexes comprise magnetic metal nanoparticles. For flow cytometry applications, the nanoparticles in the complexes comprise semiconductor nanoparticles capable of emitting a wavelength when excited with an energy source.

Another application for the complexes includes local heating. The complexes of the present invention can be coupled to a biological molecule in order to induce a local increase in temperature. For example, complexes comprising gold nanoparticles can be attached to DNA by, for example, the use of functionalized micelles.

The complexes comprising metal nanoparticles can be heated, for example, by placing the complexes in an alternating magnetic field which increase the temperature of the metal nanoparticle. The increase in temperature induces, for example, denaturation of the biological molecule while leaving the surrounding biological molecules relatively unaffected. Thus, local heating can be applied to, for example, hybridization reactions of biological molecules.

Local heating can also be applied to drug delivery. For example, water soluble complexes can comprise a hydrophobic drug encapsulated in a micelle comprising a metal particle (e.g., gold) in the inner core. The metal particle can be heated to allow for release of the drug from the complex. Therefore, the release of the drug from the complexes can be controlled in vivo.

Further applications for the complexes include, for example, nuclear magnetic resonance imaging, bar codes, and labeling biological molecules in microarrays, Northern Blots, Southern Blots, and Western Blots, etc.

Production of Complexes

The process of coating a nanoparticle with hydrophobic ligands is known to those in the art. For example, Murray et al. *J. Am. Chem. Soc.* (1993) 115:8706, Hines et al. *J. Phys. Chem.* (1996) 100:468, and U.S. Pat. No. 6,319,426 B1 to Bawendi et al. describe coating a CdSe/ZnS core/shell nanoparticle with TOPO. The relevant portions of the above cited references are hereby incorporated by reference.

The coated-nanoparticle can be encapsulated in a micelle by any method known to those skilled in the art. For example, the coated-nanoparticles can be incorporated in a micelle by chemical conjugation or by physical entrapment through dialysis or emulsification techniques. In both methods, the formation of the micelle and the encapsulation of the coated-nanoparticle typically result from the gain in the standard entropy of micellization.

Emulsification techniques comprise, for example, placing coated-nanoparticles in a non-polar solvent comprising hydrophobic and hydrophilic moieties. Examples of non-polar solvents include chloroform and hexane. Water is added and the solution mixed. The non-polar solvent is then evaporated, for example, by heat, to yield water soluble complexes of micelle encapsulated coated-nanoparticles.

In the method summarized above, it is not necessary to add water to the solution before evaporation of the non-polar solvent. Thus, the non-polar solvent may be evaporated first, followed by addition of water. However, the inventors have found that addition of water, followed by evaporation of the non-polar solvent, yields smaller complexes, and is therefore the preferred encapsulation process.

An example of the preferred process is disclosed in U.S. Pat. No. 6,319,426 B1 to Bawendi et al. in column 22, lines 50-67, which teaches a method for preparing a water soluble complex comprising a TOPO-coated CdSe/ZnS semiconductor nanoparticle encapsulated in a surfactant. The method of Bawendi et al. can be adapted to make complexes according to the present invention. The above-cited portion of U.S. Pat. No. 6,319,426 B1 is hereby incorporated by reference.

Dialysis can also be utilized to encapsulate coated-nanoparticles. The coated-nanoparticles and non-polar solvent comprising hydrophobic and hydrophilic moieties are placed in a dialysis bag and dialyzed against water to yield water soluble complexes.

EXAMPLES

Example 1

Synthesis of Water Soluble Complexes with PEG, Molecular Weight of 2000

CdSe/ZnS core/shell nanoparticles were coated with the hydrophobic ligand TOPO following standard procedure described in the literature (Murray et al. *J. Am. Chem. Soc.* (1993) 115:8706; Hines et al. *J. Phys. Chem.* (1996) 100: 468). The coated nanoparticles were stored at room temperature in hexane at 170 mg/ml.

To form the water soluble complex, 100 μl of CdSe/ZnS nanoparticles were precipitated with methanol and dried under vacuum. The nanoparticle precipitate was then suspended in 1 ml of a chloroform solution containing a total of $5.5 \times 10^{-6}$ mole of phospholipids, of which 40% by weight was 1,2-dipalmitoyl-sn-glycero-3-phosphoethanolamine-N-[methoxy(polyethylene glycol)-2000 (mPEG-2000-PE) and 60% by weight was 1,2-dipalmitoryl-glycero-3-phosphocholine.

After complete evaporation of the chloroform, the residue was heated at 80° C. Next, 1 ml of water was added to obtain an optically clear solution containing PEG-PE/PC micelles. The solution contains both empty micelles and micelles containing the nanoparticles.

The empty micelles were separated from the micelles containing the nanoparticle (i.e., water soluble complexes) with ultracentrifugation at 500,000 g for two hours. The micelles containing the nanoparticles formed a pellet while the empty micelles stayed in suspension. The supernatant was discarded and the water soluble complexes were suspended in water.

In transmission electron microscopy (TEM), the water soluble complexes are spherical and fairly monodisperse (FIGS. 1A and B). The inner core of the complex was approximately 6.4 nm in diameter. The size of the water soluble complex ranged from 10 to 15 nm. This size was similar to the diameter of empty micelles formed with 100% by weight of PEG(2000)-PE. Thus, the encapsulation of the semiconductor nanoparticle inside the micelle does not significantly perturb the geometry or size of the micelle.

Furthermore, in an aqueous solution, the complex is stable for months. The water soluble complexes were stable over a broad range of salt concentrations. In addition, the optical properties of the nanoparticles encapsulated in micelles was extremely well preserved.

Example 2

Synthesis of Water Soluble Complexes with PEG, Molecular Weight of 2000

CdSe/ZnS core/shell nanoparticles were coated with the hydrophobic ligand TOPO following standard procedure described in the literature (Murray et al. *J. Am. Chem. Soc.* (1993) 115:8706; Hines et al. *J. Phys. Chem.* (1996) 100: 468). The coated nanoparticles were stored at room temperature in hexane at 170 mg/ml.

To form the water soluble complex, 100 μl of CdSe/ZnS nanoparticles were precipitated with methanol and dried under vacuum. The nanoparticle precipitate was then suspended in 1 ml of a chloroform solution containing a total of $5.5 \times 10^{-6}$ mole of phospholipids, of which 40% by weight was 1,2-dipalmitoyl-sn-glycero-3-phosphoethanolamine-N-[methoxy(polyethylene glycol)-2000 (mPEG-2000-PE) and 60% by weight was 1,2-dipalmitoryl-glycero-3-phosphocholine.

Water was added to the solution containing PEG-PE/PC micelles. Next, the solution was heated to evaporate the chloroform. The solution contains both empty micelles and micelles containing the nanoparticles.

The empty micelles were separated from the micelles containing the nanoparticle (i.e., water soluble complexes) with ultracentrifugation at 500,000 g for two hours. The micelles containing the nanoparticles formed a pellet while the empty micelles stayed in suspension. The supernatant was discarded and the water soluble complexes were suspended in water.

In transmission electron microscopy (TEM), the water soluble complexes are spherical and fairly monodisperse. The inner core of the complex was approximately 6.4 nm in diameter. The size of the water soluble complex ranged from 10 to 15 nm. This size was similar to the diameter of empty micelles formed with 100% by weight of PEG(2000)-PE. Thus, the encapsulation of the semiconductor nanoparticle inside the micelle does not significantly perturb the geometry or size of the micelle.

Furthermore, in an aqueous solution, the complex is stable for months. The water soluble complexes were stable over a broad range of salt concentrations. In addition, the optical properties of the nanoparticles encapsulated in micelles was extremely well preserved.

Example 3

Synthesis of Water Soluble Complexes with Various Molecular Weight of PEG

Water soluble complexes were formed with PEG having a molecular weight of 550 or 5000 according to the procedure described in Example 1 above. The use of mPEG550-PE or mPEG-5000-PE yielded complexes similar in shape to those obtained from mPEG-2000-PE.

Example 4

Attachment of Biological Molecules to Water Soluble Complexes

To explore the use of the water soluble complexes in vitro as fluorophores for the detection of, for example, specific nucleic acids or proteins, the water soluble complexes were attached to DNA.

In particular, during formation of the micelle, up to 50% by weight of the PEG-PE phospholipids in Example 1 above, were replaced with amino PEG-PE (1,2,-distearoyl-sn-glycero-3-phosphoethanolamine-N-[amino(polyethylene glycol) 2000] (Avanti Polar Lipids, Inc.). The resulting micelles have primary amino groups on their outer surfaces.

Thiol modified DNA was then covalently coupled to the primary amines using SMCC as an heterobifunctional coupler. Non-coupled DNA was removed by ultracentrifugation.

Figure 2A:
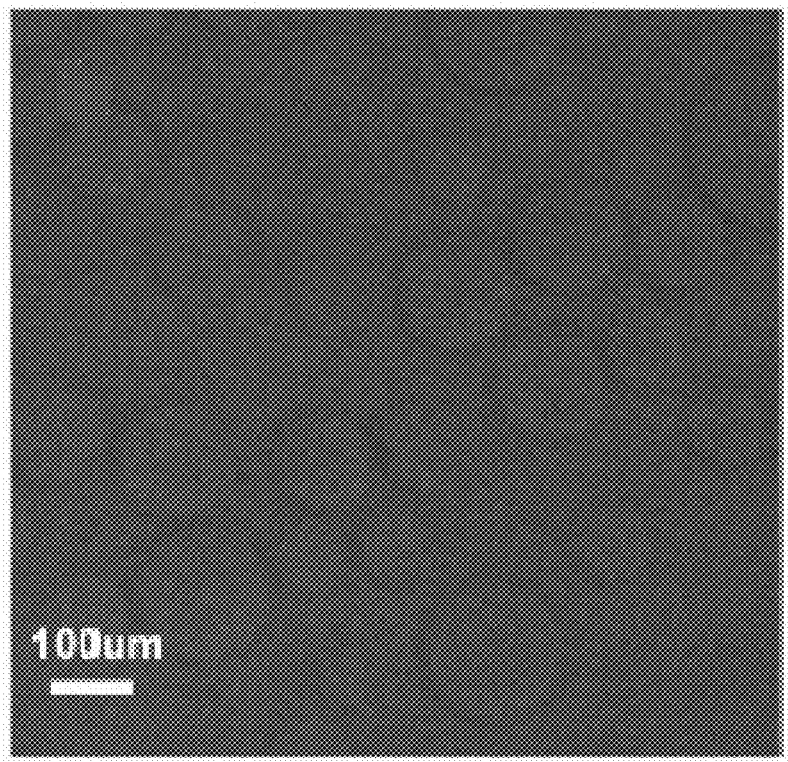
FIG. 2: Hybridization of water soluble complexes conjugated with DNA to surface bound single-stranded DNA (ss-DNA). Biotin-modified DNA (20 bases, ss-DNA) was attached to streptavidin modified 4% agarose beads. A PBS solution containing water soluble complexes conjugated with 20 base long ss-DNA was added to the agarose bead solution and incubated at room temperature for more than 10 min. After rinsing once with PBS, the beads fluorescence was measured with an optical microscope. (A) The oligonucleotides bound to the agarose beads are not complementary to the oligonucleotides conjugated to the water soluble complexes. (B) The oligonucleotides bound to the agarose beads are complementary to the oligonucleotides conjugated to the water soluble complexes.
Figure 2B:
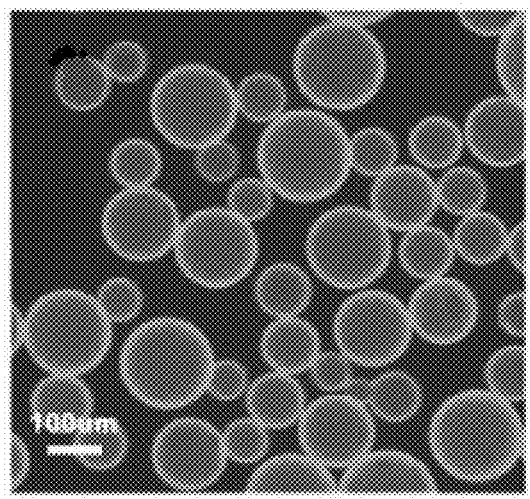

Oligonucleotide nanoparticle-micelle complexes bound specifically to complementary DNA, immobilized on 4% agarose beads, but not to non-complementary oligonucleotides (FIGS. 2A and B). Hybridization occurred very rapidly; incubation times as low as 10 minutes yielded highly fluorescent agarose beads (FIG. 2B). Thus, the nanoparticle-micelle complexes do not prevent specific hybridization of the oligonucleotides to DNA targets.

The water soluble complexes also exhibit excellent fluorescence. The fluorescence signal to background ratio was above 150, compared to about four for silica-coated semiconductor nanoparticles.

The above approach offered excellent conjugation yields. When the number of DNA conjugated water soluble complexes was smaller than the number of binding sites, all the DNA-conjugated complexes were immobilized on the agarose beads. Therefore, at least one DNA molecule was conjugated to each micelle.

Example 5

Figure 2C:
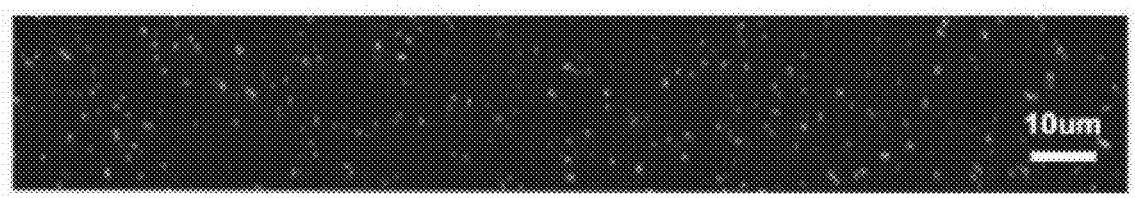
Figure 2D:
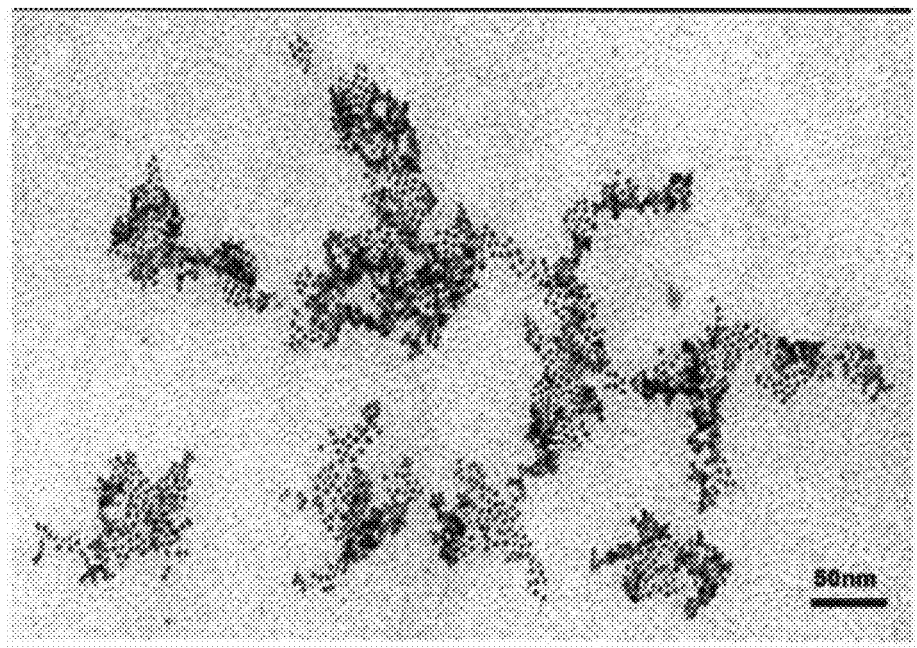

Efficiency of Hybridization of Biomolecules Conjugated to Water Soluble Complexes To verify the excellent efficiency of the hybridization of the DNA-conjugated complexes to complementary sequence, directed assembly was performed. Equal amounts of two batches of water soluble complexes, each conjugated with a complementary oligonucleotide, were mixed together. After incubation for one hour at room temperature, fluorescent aggregates were visible under the microscope (FIG. 2C). TEM confirmed that these aggregates, which ranged is size from 0.2 to 2 µm, were formed (FIG. 2D).

Example 6

Determination of Cell Lineage

Figure 3A:
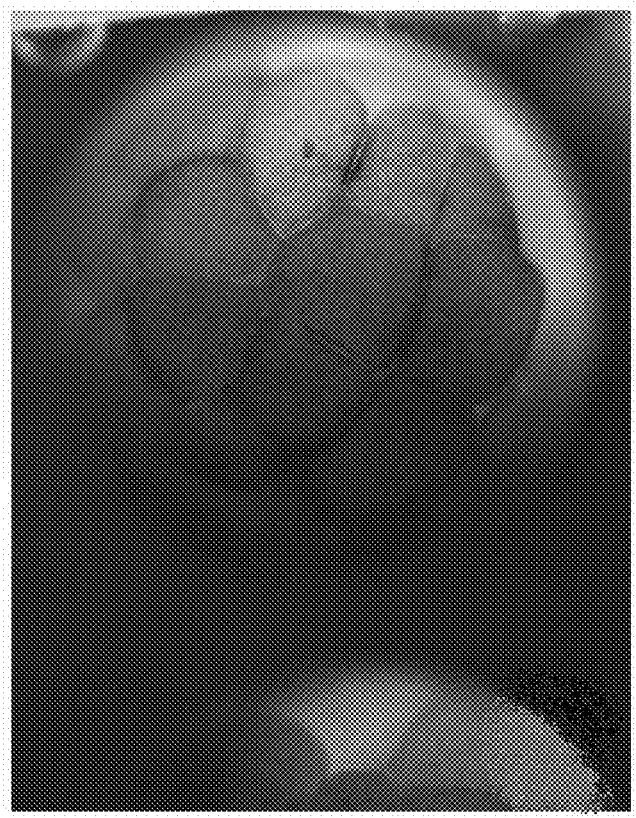
FIG. 3: Water soluble complexes labeling of *Xenopus* embryos at several different stages and specific intracellular localization of complexes. Embryos were microinjected and cultured until various stages of development were reached. The embryos were imaged using an axioplan Zeiss microscope under direct UV excitation. For embryos (A) to (D), transmitted and fluorescent images have been superimposed. (A) Injection of one cell out of an eight cell stage embryo results in labeling of the single blastomeres. (B) Same embryo as in (A) shown one hour later. The daughter cells of the injected blastomere are labeled. (C) and (D) show two neurula embryos, which were injected in a single cell at the eight cell stage in the animal pole. (E) The nanoparticle-micelle complexes are localized in the nucleus during mid-blastula stages. The localization disappears in later stages of development. (F) Autofluorescence emanating from the gut of a tadpole. No complexes were injected in the embryo. (G) Detection of fluorescence of nanoparticle-micelle complexes in highly autofluorescent backgrounds, such as the gut of an injected embryo. (H) Intracellular labeling of an axon (arrow) and somites at tadpole stage 40. The complexes migrate into axons all the way to growth cones. In the somites, the complexes appears to localize in subcellular structures.
Figure 3B:
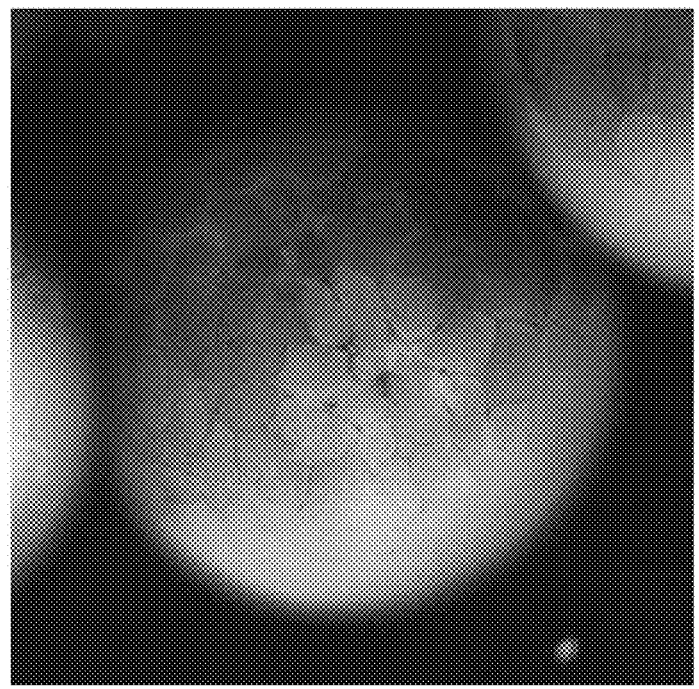
Figure 3C:
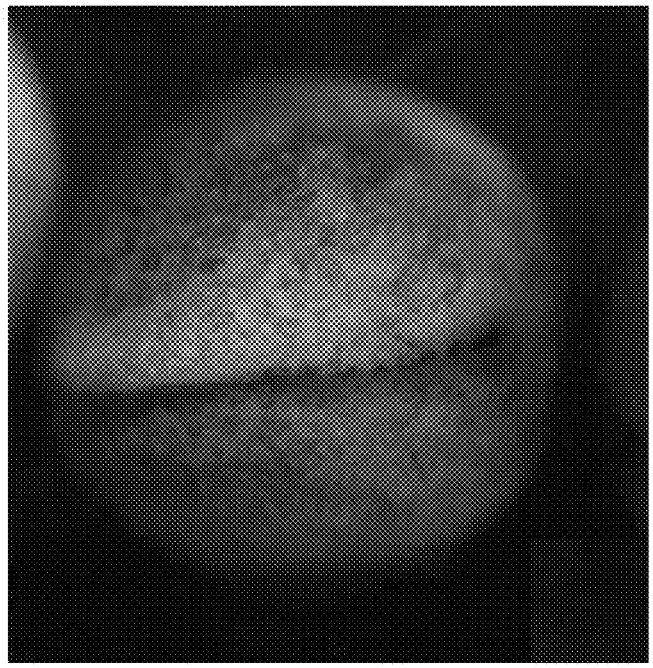
Figure 3D:
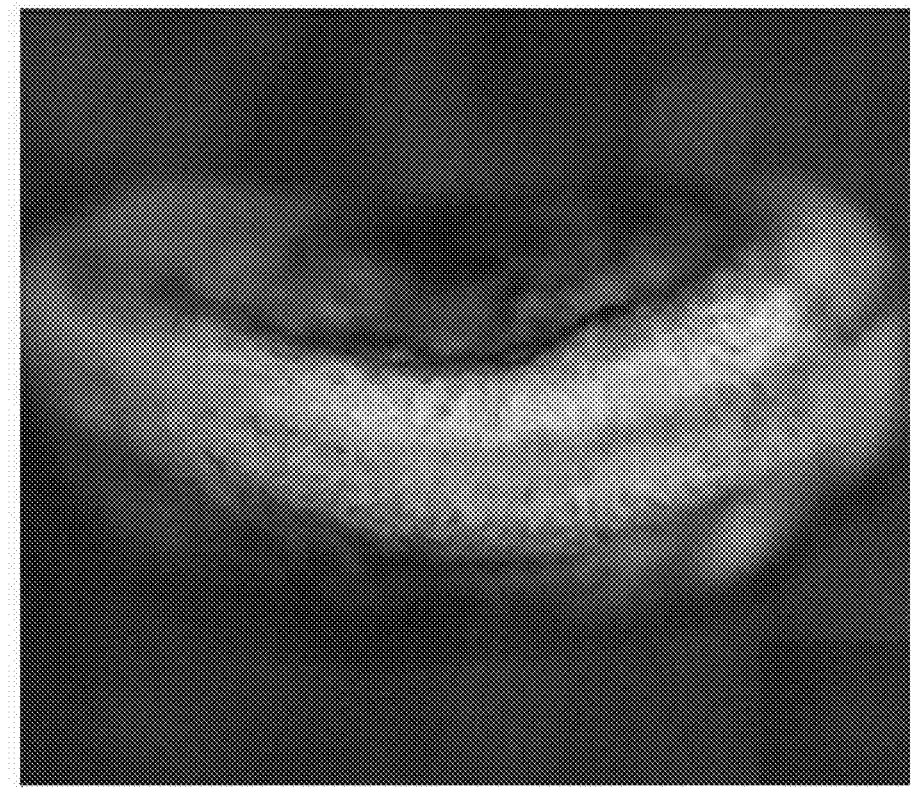
Figure 3E:
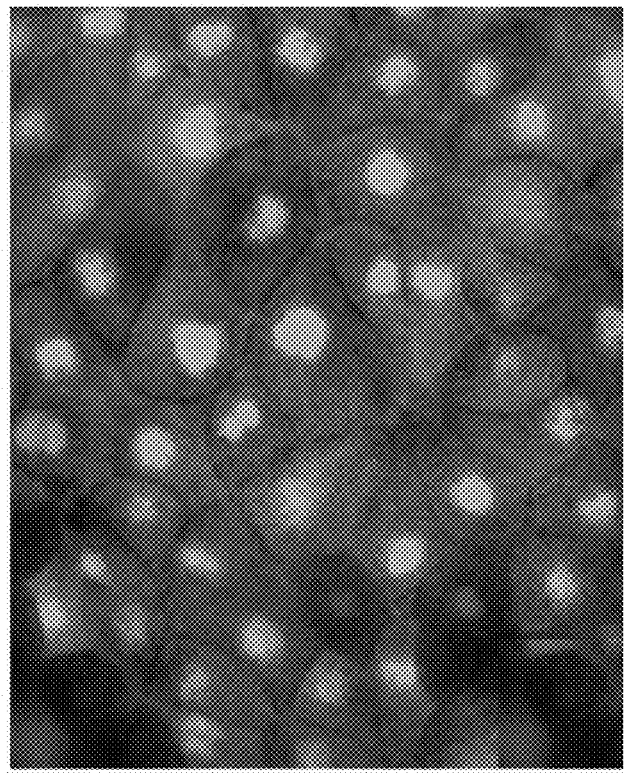

To test the in vivo usefulness of the nanoparticle-micelles, one cell from a two-cell Xenopus embryo was microinjected with the nanoparticle-micelles. Fluorescence of the nanoparticle was confined only to the progeny of the injected cell (e.g., only half of the cells of the embryo was labeled). Further, when the nanoparticle-micelles were injected later in embryogenesis into individual blastomers, the nanoparticle-micelles were confined to the progeny of the injected cells (FIGS. 3A and B). Thus, the nanoparticle-micelle tracer is autonomous.

The fluorescence is visible very early during development (FIG. 3A) despite pigmentation and strong background fluorescence. This is a significant advantage over other tracers, such as green fluorescent protein (GFP), which requires time for GFP (injected as RNA) to be expressed at levels detectable in vivo.

Figure 3F:
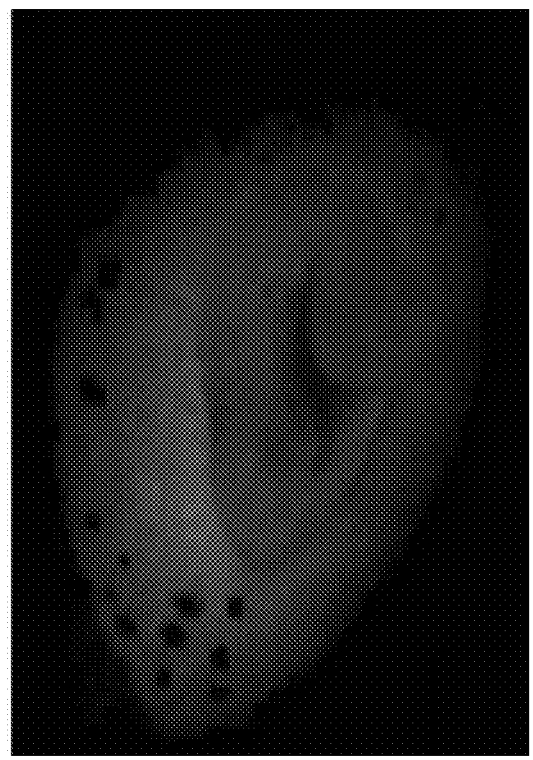
Figure 3G:
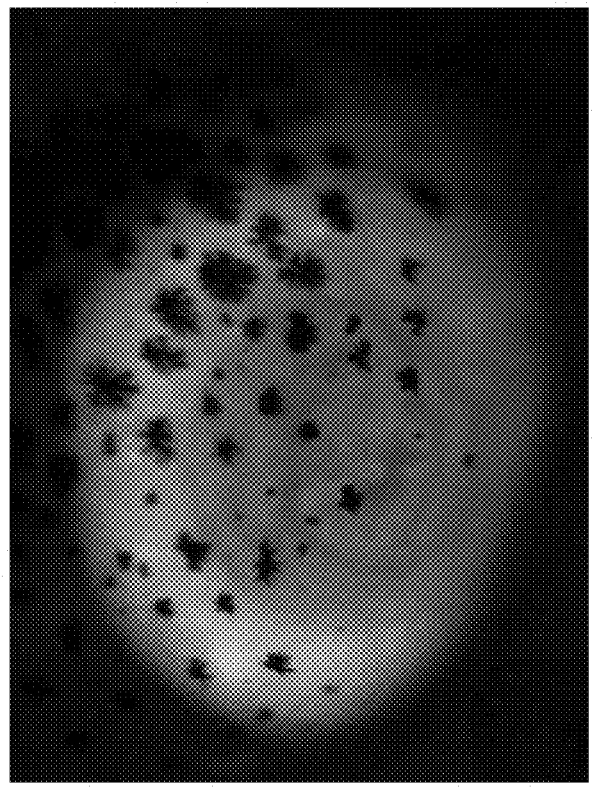
Figure 3H:
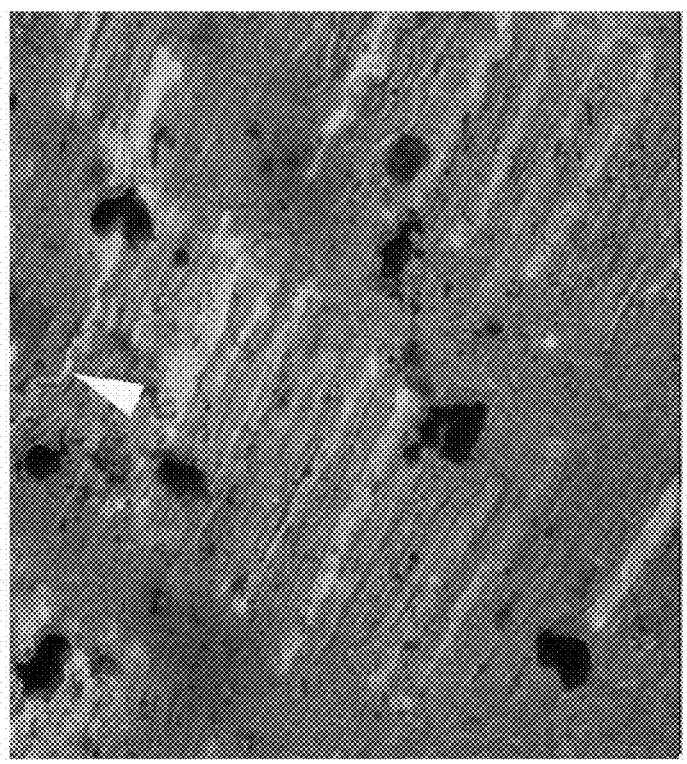

The nanoparticle-micelle exhibit very low activity or toxicity in vivo. The phenotype of the injected embryos were similar to that of the uninjected embryos. After four days of embryonic development, the nanoparticle-micelles did not exhibit any visible aggregation. Furthermore, the fluorescence of the nanoparticle-micelles was still detectable at the tadpole stage of the Xenopus organism, even in high background regions such as the embryo guts (FIGS. 3F and G). Moreover, all embryonic cell types, including neurons and axonal tracks (FIG. 3H), can be labeled with the nanoparticle-micelle complexes, without visible segregation.

Example 7

Stability of Fluorescence of Nanoparticle-Micelles

To determine if the nanoparticle-micelles are more resistant to photo-bleaching than other fluorochromes, the quenching of the fluorescence between a membrane-bound form of GFP and the nanoparticle-micelles were compared.

Figure 4:
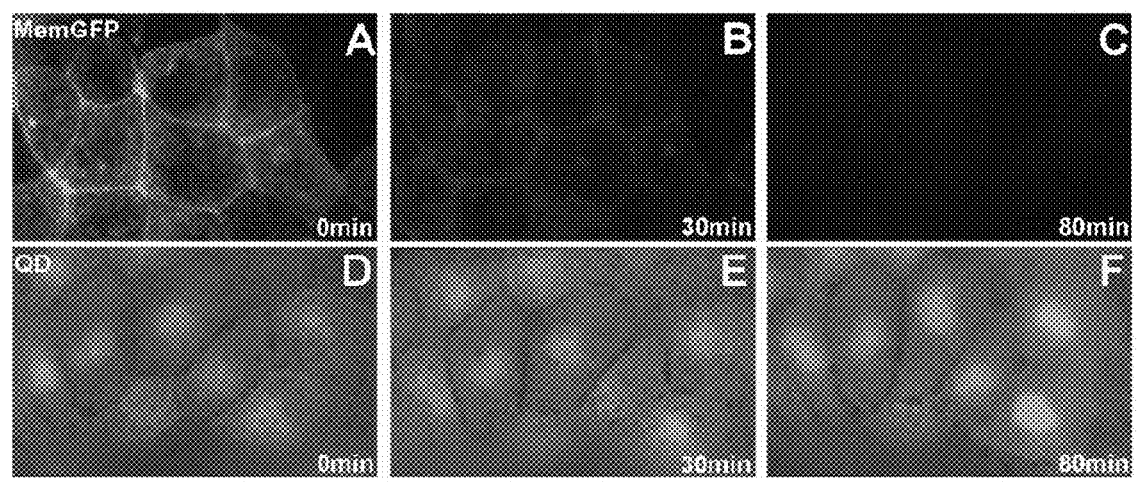
FIG. 4: Resistance to photobleaching of water soluble complexes compared to green fluorescent protein (GFP). (A) through (C) are consecutive images of membrane-GFP expressed in *Xenopus* ectoderm (animal pole). (D) through (F) are consecutive images of nanoparticle-micelle complexes (quantum dots, QD) injected in *Xenopus* animal pole blastomers. (G) and (H) are graphs representing the fluorescence of GFP and complexes, respectively, through an 80 minute period during which both fluorophores were exposed to continuous excitation UV light.
Figure 4:
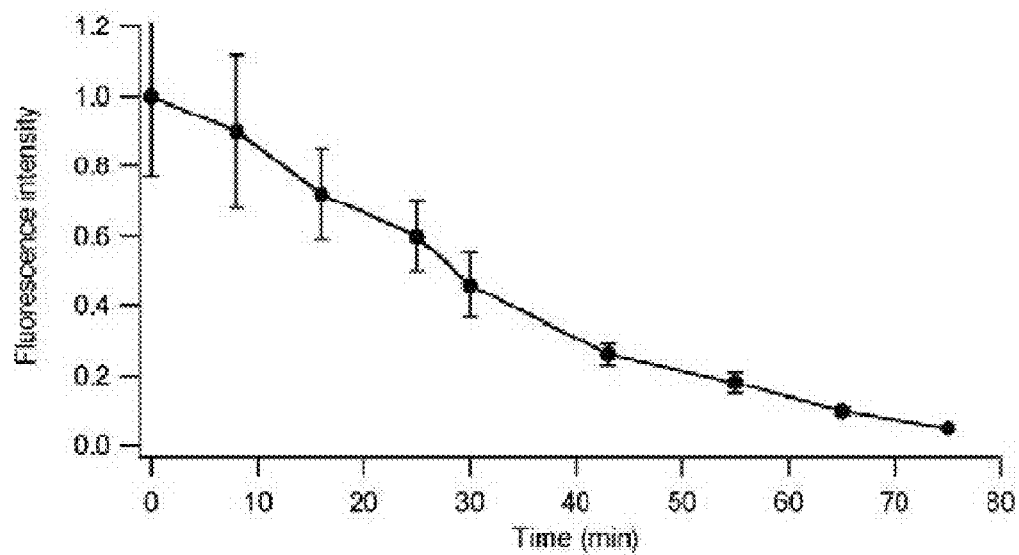
Figure 4:
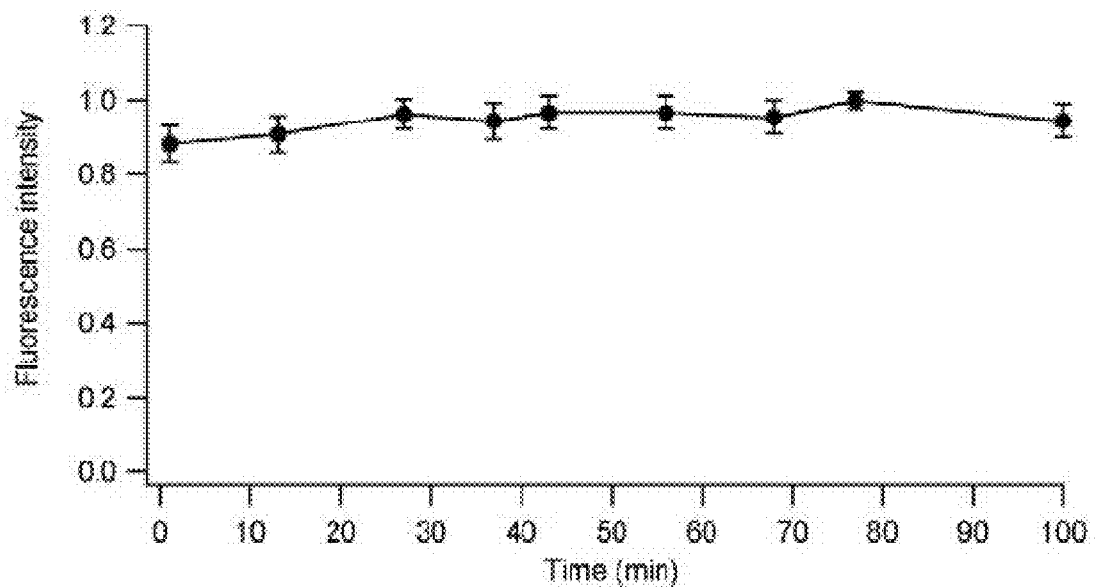

Nanoparticle-micelles were injected into a blastomer of an Xenopus embryo. RNA encoding the membrane GFP was microinjected into the blastomer of a sibling embryo in a similar stage of development. The fluorescence was examined in the embryos (FIGS. 4A-F). After 80 minutes of constant UV illumination under the compound microscope, the nanoparticle-micelle fluorescence intensity remained stable (FIG. 4F), whereas the GFP was completely photo-bleached (FIG. 4C). FIGS. 4G and 4H is a graph of the fluorescence intensity of GFP (FIG. 4G) and the nanoparticle-micelle complexes (FIG. 4H) over time.

Thus, nanoparticle-micelles are more resistant to photobleaching than conventional biolabels.

What we claim is:

1. A water soluble complex comprising
   an inner core of a metal or semi-conductor nanoparticle;
   the nanoparticle being coated with a hydrophobic ligand;
   the coated nanoparticle being encapsulated in a micelle comprising 1,2-di(fatty acyl)-sn-glycero-3-phosphoethanolamine-N-poly(ethylene glycol) (PEG-PE) the micelle comprises a chemical moiety capable of combining with biological molecules, and wherein the complex does not aggregate in vivo for at least four days.

2. A complex according to claim 1, wherein the chemical moiety is amino, thiol, carboxyl, hydroxyl, succinimidyl, maleimide, biotin, aldehyde, or nitrilotriacetic moiety.

3. A complex according to claim 1, wherein the biological molecule is DNA or RNA.

4. A complex according to claim 1, wherein the biological molecule comprises an amino acid sequence.

5. A complex according to claim 1, wherein the fatty acyl moiety comprises a chain having a minimum of 12 carbon atoms.

6. A complex according to claim 1, wherein the fatty acyl moiety comprises a chain having a minimum of 16 carbon atoms.

7. A complex according to claim 1, wherein the fatty acyl moiety comprises a chain having a maximum of 18 carbon atoms.

8. A complex according to claim 1, wherein the fatty acyl groups are dipalmitoyl groups.

9. A complex according to claim 1, wherein the nanoparticle is a semiconductor nanoparticle.

10. A complex according to claim 9, wherein the semiconductor nanoparticle comprises a group II-VI semiconductor.

11. A complex according to claim 10, wherein the group II-VI semiconductor is MgS, MgSe, MgTe, CaS, CaSe, CaTe, SrS, SrSe, SrTe, BaS, BaTe, BaTe, ZnS, ZnSe, ZnTe, CdS, CdSe, CdTe, HgS, HgSe, or HgTe and mixtures thereof.

12. A complex according to claim 9, wherein the nanoparticle is in a core/shell configuration.

13. A complex according to claim 12, wherein the core comprises MgS, MgSe, MgTe, CaS, CaSe, CaTe, SrS, SrSe, SrTe, BaS, BaTe, BaTe, ZnS, ZnSe, ZnTe, CdS, CdSe, CdTe, HgS, HgSe, HgTe, GaAs, GaN, GaP, GaSb, InGaAs, InP, InN, InSb, InAs, AlAs, AlP, AlSb, AlS, PbS, PbSe, Ge, Si, or mixtures thereof, and the shell comprises ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AN, AlP, AlSb, or mixtures thereof.

14. A complex according to claim 1, wherein the maximum average diameter of the micelles is 40 nm.

15. A complex according to claim 1, wherein the maximum average diameter of the micelles is 35 nm.

16. A complex according to claim 1, wherein the micelle has an minimum average diameter of approximately 9 nm and a maximum average diameter of approximately 15 nm.

17. A complex according to claim 1, wherein the hydrophobic ligand coats the nanoparticle non-covalently.

18. A complex according to claim 17, wherein the hydrophobic ligand is trioctylphosphine oxide (TOPO).

19. A complex according to claim 1, wherein the inner core of the complex comprises a minimum of one and a maximum of 1000 nanoparticles.

20. A complex according to claim 1, wherein the inner core of the complex comprises a minimum of one and a maximum of 500 nanoparticles.

21. A complex according to claim 1, wherein the inner core of the complex comprises a minimum of one and a maximum of 100 nanoparticles.

22. A complex according to claim 1, wherein the inner core of the complex comprises a minimum of one and a maximum of 50 nanoparticles.

23. A complex according to claim 1, wherein the inner core of the complex comprises a minimum of one and a maximum of 20 nanoparticles.

24. A complex according to claim 1, wherein the inner core of the complex comprises one nanoparticle.

25. A complex according to claim 1, wherein the inner core of the complex comprises at least two different nanoparticles.

26. A complex according to claim 1, wherein the inner core of the complex comprises nanoparticles having at least two different average diameters.

27. A conjugate comprising a complex according to claim 1 and a biological molecule.

28. A conjugate according to claim 27, wherein the biological molecule is DNA or RNA.

29. A conjugate according to claim 27, wherein the biological molecule comprises an amino acid sequence.

* * * * *